(12) United States Patent
Bui et al.

(10) Patent No.: US 8,883,132 B2
(45) Date of Patent: *Nov. 11, 2014

(54) COSMETIC COMPOSITIONS COMPRISING A POLAR MODIFIED POLYMER AND A TACKIFIER

(75) Inventors: Hy Si Bui, Piscataway, NJ (US); Mohamed Kanji, Edison, NJ (US); Balanda Atis, Newark, NJ (US); Susan Halpern, Paramus, NJ (US); Florentina Pavel, Hillsborough, NJ (US)

(73) Assignee: L'Oreal, Paris (FR)

( * ) Notice: Subject to any disclaimer, the term of this patent is extended or adjusted under 35 U.S.C. 154(b) by 28 days.

This patent is subject to a terminal disclaimer.

(21) Appl. No.: 12/824,946

(22) Filed: Jun. 28, 2010

(65) Prior Publication Data

US 2011/0020259 A1    Jan. 27, 2011

Related U.S. Application Data

(63) Continuation of application No. PCT/US2008/088090, filed on Dec. 23, 2008.

(60) Provisional application No. 61/017,455, filed on Dec. 28, 2007, provisional application No. 61/017,439, filed on Dec. 28, 2007, provisional application No. 61/017,384, filed on Dec. 28, 2007.

(51) Int. Cl.
| | |
|---|---|
| *A61K 31/74* | (2006.01) |
| *A61K 31/00* | (2006.01) |
| *A61K 8/72* | (2006.01) |
| *A61K 8/02* | (2006.01) |
| *A61Q 1/06* | (2006.01) |
| *A61Q 5/00* | (2006.01) |
| *A61Q 7/00* | (2006.01) |
| *A61K 8/81* | (2006.01) |
| *A61K 8/06* | (2006.01) |
| *A61Q 1/10* | (2006.01) |
| *A61Q 1/04* | (2006.01) |
| *A61K 8/90* | (2006.01) |

(52) U.S. Cl.
CPC ............. *A61K 8/06* (2013.01); *A61K 8/8111* (2013.01); *A61K 8/8117* (2013.01); *A61Q 1/10* (2013.01); *A61Q 1/04* (2013.01); *A61K 8/90* (2013.01)
USPC ............. 424/78.08; 424/401; 424/70.11; 424/78.03; 424/64; 424/78.2

(58) Field of Classification Search
USPC .......... 424/78.08, 401, 70.11, 78.03, 64, 78.2
See application file for complete search history.

(56) References Cited

U.S. PATENT DOCUMENTS

| | | | | |
|---|---|---|---|---|
| 3,088,876 | A * | 5/1963 | Buth ............................ | 424/64 |
| 3,560,455 | A | 2/1971 | Heilman et al. | |
| 5,998,547 | A * | 12/1999 | Hohner ........................ | 525/301 |
| 7,884,158 | B2 * | 2/2011 | Bui et al. ..................... | 525/64 |
| 8,540,973 | B2 | 9/2013 | Bui et al. | |
| 8,551,459 | B2 | 10/2013 | Bui et al. | |
| 8,551,460 | B2 | 10/2013 | Bui et al. | |
| 8,551,461 | B2 | 10/2013 | Bui et al. | |
| 8,551,465 | B2 | 10/2013 | Bui et al. | |
| 8,551,466 | B2 | 10/2013 | Bui et al. | |
| 8,562,961 | B2 | 10/2013 | Bui et al. | |
| 8,597,621 | B2 | 12/2013 | Bui et al. | |
| 8,597,626 | B2 | 12/2013 | Bui et al. | |
| 8,609,079 | B2 | 12/2013 | Bui et al. | |
| 8,647,611 | B2 | 2/2014 | Bui et al. | |
| 8,652,451 | B2 | 2/2014 | Bui et al. | |
| 8,663,609 | B2 | 3/2014 | Bui et al. | |
| 8,663,667 | B2 | 3/2014 | Bui et al. | |
| 2004/0234612 | A1 * | 11/2004 | Blin et al. ................... | 424/489 |
| 2005/0008597 | A1 | 1/2005 | Furukawa et al. | |
| 2005/0228115 | A1 * | 10/2005 | Auguste et al. ............. | 524/505 |
| 2006/0084764 | A1 * | 4/2006 | Hanna et al. ................ | 525/242 |
| 2006/0188459 | A1 * | 8/2006 | Heinrichs et al. ............ | 424/63 |
| 2007/0031361 | A1 * | 2/2007 | Herrmann et al. .......... | 424/70.11 |
| 2007/0149703 | A1 | 6/2007 | Caprasse et al. | |
| 2007/0212317 | A1 * | 9/2007 | Atis et al. ................... | 424/70.11 |
| 2007/0258923 | A1 * | 11/2007 | Bui et al. ..................... | 424/63 |
| 2007/0258924 | A1 * | 11/2007 | Bui et al. ..................... | 424/64 |
| 2007/0258925 | A1 * | 11/2007 | Bui et al. ..................... | 424/64 |
| 2007/0258932 | A1 * | 11/2007 | Bui et al. ................... | 424/70.11 |
| 2007/0258933 | A1 * | 11/2007 | Bui et al. ................... | 424/70.11 |
| 2007/0258934 | A1 * | 11/2007 | Bui et al. ................... | 424/70.11 |
| 2008/0171006 | A1 * | 7/2008 | Bui et al. ..................... | 424/64 |
| 2008/0171007 | A1 * | 7/2008 | Bui ............................... | 424/64 |
| 2008/0175808 | A1 * | 7/2008 | Pavel .......................... | 424/70.7 |
| 2010/0330012 | A1 * | 12/2010 | Bui et al. ..................... | 424/61 |
| 2010/0330015 | A1 * | 12/2010 | Bui et al. ..................... | 424/64 |
| 2010/0330016 | A1 * | 12/2010 | Bui et al. ..................... | 424/64 |
| 2010/0330017 | A1 * | 12/2010 | Bui et al. ..................... | 424/64 |
| 2010/0330022 | A1 * | 12/2010 | Bui et al. ................... | 424/78.02 |
| 2010/0330024 | A1 * | 12/2010 | Bui et al. ................... | 424/78.03 |
| 2011/0020254 | A1 * | 1/2011 | Bui et al. ..................... | 424/63 |
| 2011/0020255 | A1 * | 1/2011 | Bui et al. ..................... | 424/64 |
| 2011/0020256 | A1 * | 1/2011 | Bui et al. ..................... | 424/64 |
| 2011/0020257 | A1 * | 1/2011 | Bui et al. ..................... | 424/64 |
| 2011/0020260 | A1 * | 1/2011 | Bui et al. ................... | 424/70.7 |
| 2011/0020261 | A1 * | 1/2011 | Bui et al. ................... | 424/70.7 |
| 2011/0021681 | A1 * | 1/2011 | Bui et al. ..................... | 524/386 |
| 2011/0021683 | A1 * | 1/2011 | Bui et al. ..................... | 524/388 |
| 2011/0038819 | A1 * | 2/2011 | Bui et al. ..................... | 424/63 |
| 2011/0150802 | A1 * | 6/2011 | Bui et al. ..................... | 424/63 |
| 2011/0150806 | A1 * | 6/2011 | Bui et al. ................... | 424/70.7 |
| 2011/0223122 | A1 * | 9/2011 | Bui et al. ..................... | 424/64 |
| 2011/0223123 | A1 * | 9/2011 | Bui et al. ................... | 424/70.7 |
| 2011/0280819 | A1 | 11/2011 | Bui et al. | |

(Continued)

FOREIGN PATENT DOCUMENTS

| | | |
|---|---|---|
| DE | 102005026278 A1 * | 10/2005 |
| JP | 2006-232831 A | 9/2006 |
| WO | WO 2005100444 A1 * | 10/2005 |

*Primary Examiner* — Abigail Fisher
(74) *Attorney, Agent, or Firm* — Oblon, Spivak, McClelland, Maier & Neustadt, L.L.P.

(57) ABSTRACT

The invention relates to a cosmetic composition comprising at least one polar modified polymer and at least one tackifier, as well as to methods of using such compositions.

18 Claims, No Drawings

(56) References Cited

U.S. PATENT DOCUMENTS

| | | |
|---|---|---|
| 2011/0280820 A1 | 11/2011 | Bui et al. |
| 2011/0286949 A1 | 11/2011 | Bui et al. |
| 2011/0286950 A1 | 11/2011 | Bui et al. |
| 2011/0286951 A1 | 11/2011 | Bui et al. |
| 2011/0286954 A1 | 11/2011 | Bui et al. |
| 2011/0293550 A1 | 12/2011 | Bui et al. |
| 2012/0003169 A1 | 1/2012 | Bui et al. |
| 2012/0004327 A1 | 1/2012 | Bui et al. |
| 2012/0020907 A1 | 1/2012 | Bui et al. |
| 2012/0107263 A1 | 5/2012 | Bui et al. |
| 2012/0171140 A1 | 7/2012 | Bui et al. |
| 2012/0219516 A1* | 8/2012 | Ramada et al. .......... 424/64 |
| 2014/0004069 A1 | 1/2014 | Bui et al. |
| 2014/0037565 A1 | 2/2014 | Bui et al. |

* cited by examiner

COSMETIC COMPOSITIONS COMPRISING A POLAR MODIFIED POLYMER AND A TACKIFIER

CROSS-REFERENCE TO RELATED APPLICATIONS

This application is a continuation of International Application No. PCT/US2008/088090, filed Dec. 23, 2008, which claims the benefit of U.S. Ser. Nos. 61/017,384, 61/017,455, and 61/017,439, all filed Dec. 28, 2007, the entire contents of which are hereby incorporated by reference.

FIELD OF THE INVENTION

The present invention generally relates to compositions for keratin materials (for example, lips, hair or eyelashes) such as, for example, mascaras and lip compositions (for example, lipsticks or lip gloss) comprising at least one polar modified polymer and at least one tackifier. Such compositions, when applied to keratin materials such as hair or eyelashes, can impart improved length, lift and/or hold to the keratin materials. Such compositions, when applied to keratin materials such as lips, can impart improved texture/feel characteristics without much gloss reduction or tackiness.

DISCUSSION OF THE BACKGROUND

Many mascaras and other cosmetic compositions have been developed for improved wear, transfer-resistance, and length/volume properties. Such properties are typically accomplished by the use of ingredients that form a film after application. Such compositions generally contain volatile solvents, which evaporate on contact with the skin or eyelashes, leaving behind a layer comprising waxes and/or resins, pigments, fillers, and actives. However, there remains a need for improved cosmetic compositions, particularly mascaras and lip compositions, which possess significantly improved appearance and/or functional cosmetic properties, particularly one or more of the properties mentioned above.

Accordingly, one aspect of the present invention is a makeup, care and/or treatment composition for keratin materials such as lips, hair or eyelashes which is able to provide significantly improved appearance and/or functional cosmetic properties to the keratin materials.

SUMMARY OF THE INVENTION

The present invention relates to compositions for keratin materials (for example, hair or eyelashes) such as mascaras comprising at least one polar modified polymer and at least one tackifier. Such compositions can further comprise at least one block copolymer and/or at least one alkyl silsesquioxane resin.

The present invention also relates to compositions for keratin materials (for example, lips) such as lipsticks, lip gloss or liquid lip compositions comprising at least one polar modified polymer and at least one tackifier. Such compositions can further comprise at least one block copolymer and/or at least one alkyl silsesquioxane resin.

The present invention also relates to methods of increasing the length, lift and/or hold of keratin materials (for example, hair or eyelashes) comprising applying to the keratin material a keratin material length-, lift- and/or hold-increasing effective amount of a composition comprising at least one polar modified polymer and at least one tackifier. Such compositions can further comprise at least one block copolymer and/or at least one alkyl silsesquioxane resin.

The present invention further relates to methods of making-up keratin materials comprising applying a keratin material making-up effective amount of a composition comprising at least one polar modified polymer and at least one tackifier to keratin materials in need of such making-up. Such compositions can further comprise at least one block copolymer and/or at least one alkyl silsesquioxane resin.

The present invention also relates to methods of increasing the lift or hold a composition provides to a keratin material (for example, hair or eyelashes) after or upon application to the keratin material comprising combining at least one polar modified polymer and at least one tackifier prior to application. Such compositions can further comprise at least one block copolymer and/or at least one alkyl silsesquioxane resin.

The present invention also relates to methods of treating or caring for keratin materials by applying compositions of the present invention to the keratin materials in an amount sufficient to treat and/or care for the keratin materials.

The present invention further relates to methods of enhancing the appearance of keratin materials by applying compositions of the present invention to the keratin materials in an amount sufficient to enhance the appearance of the keratin materials.

The present invention also relates to methods of making a composition comprising mixing at least one polar modified polymer and at least one tackifier to form a composition. Such compositions can further comprise at least one block copolymer and/or at least one alkyl silsesquioxane resin.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Water-insoluble," as used herein, means that the reaction product retains its structure and does not solubilize upon exposure to water.

The compositions and methods of the present invention can comprise, consist of, or consist essentially of the essential elements and limitations of the invention described herein, as well as any additional or optional ingredients, components, or limitations described herein or otherwise useful.

In accordance with the present invention, the "hardness" of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf, including all ranges and subranges therebetween.

This hardness is measured in one of two ways. A first test for hardness is according to a method of penetrating a probe into the composition and in particular using a texture analyzer (for example TA-XT21 from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

Polar Modified Polymer

According to the present invention, compositions comprising at least one polar modified polymer are provided. "Polar modified polymer" as used herein refers to "oil-soluble polar modified polymers" and/or "oil-soluble high carbon polar modified polymers."

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic:unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemcial Co., poly(ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the oil soluble polar modified polymer(s) represent from about 1% to about 20% of the total weight of the composition, more preferably from about 3% to about 17% of the total weight of the composition, and most preferably from about 5% to about 15%, including all ranges and subranges therebetween.

Oil-Soluble High Carbon Polar Modified Polymer

According to the present invention, compositions comprising at least one oil-soluble high carbon polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil. "High carbon" means more than 20 carbon atoms.

Suitable monomers for the hydrophobic homopolymers and/or copolymers include, but are not limited to, cyclic, linear or branched, substituted or unsubstituted, C22-C40 compounds such as, C22-C28 compounds, C24-C26 compounds, C26-C28 compounds, and C30-C38 compounds, including all ranges and subranges therebetween. Preferably, the monomers are C24-26 compounds, C26-C28 compounds or C30-C38 compounds.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to preferred embodiments, the oil-soluble high carbon polar modified polymer is a wax. Also preferably, the oil-soluble high carbon polar modified polymer wax has one or more of the following properties:

a weight-average molecular weight Mw of less than or equal to 30 000 g/mol, preferably of 500 to 10 000 g/mol and particularly preferably of 1000 to 5,000 g/mol, including all ranges and subranges therebetween;

a number-average molecular weight Mn of less than or equal to 15 000 g/mol, preferably of 500 to 12 000 g/mol and particularly preferably of 1000 to 5000 g/mol, including all ranges and subranges therebetween;

a molar mass distribution Mw/Mn in the range from 1.5 to 10, preferably from 1.5 to 5, particularly preferably from 1.5 to 3 and especially preferably from 2 to 2.5, including all ranges and subranges therebetween; and/or a crystallinity of 8% to 60%, preferably 9% to 40%, and more preferably 10% to 30%, including all ranges and subranges therebetween, as determined by differential scanning calorimetry.

According to preferred embodiments relating to a copolymer wax, it is preferable to have, based on the total weight of the copolymer backbone, 0.1 to 30% by weight of structural units originating from the one monomer and 70.0 to 99.9% by weight of structural units originating from the other monomer.

Waxes of the present invention can be based upon homopolymers or copolymers made, for example, by the process described in EP 571 882, the entire contents of which is hereby incorporated by reference. Suitable preparation processes include, for example, suspension polymerization, solution polymerization and gas-phase polymerization of olefins in the presence of catalysts, with polymerization in the monomers also being possible.

Oil-soluble high carbon polar modified polymer wax can be produced in a known manner from the hompopolymers and copolymers described above by oxidation with oxygen-containing gases, for example air, or by graft reaction with polar monomers, for example maleic acid or acrylic acid or derivatives of these acids. The polar modification of polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable oil-soluble high carbon polar modified polymer waxes include, but are not limited to, homopolymers and/or copolymers of C24, C25 and/or C26 groups, copolymers C26, C27 and/or C28 groups, or copolymers of C30-C38 groups, which have been modified with hydrophilic units such as, for example, maleic anhydride, acrylate, methacrylate, polyvinylpyrrolidone (PVP), etc. Preferably, the oil-soluble high carbon polar modified polymer wax has from about 5% to about 30% hydrophilic units, more preferably from about 10% to about 25% hydrophilic units by weight with respect to the weight of the wax, including all ranges and subranges therebetween. Particularly preferred hydrophilically modified waxes are C26, C27 and/or C28 homopolymers and copolymers which have been modified with maleic anhydride units.

Particularly preferred oil-soluble high carbon polar modified polymer waxes for use in the present invention are C26-C28 alpha olefin maleic acid anhydride copolymer waxes commercially available from Clariant under the trade name LICOCARE or LICOCENE. Specific examples of such waxes include products marketed by Clariant under the LicoCare name having designations such as CM 401, which is a maleic anhydride modified wax having a Mw of 2025 and a crystallinilty of 11%, C30-C38 olefin/isopropylmaleate/maleic anhydride copolymer sold by Baker Hughes under the name Performa® V 1608, and C24-C26 alpha olefin acrylate copolymer wax commercially available from Clariant under the trade name LICOCARE CA301 LP3346 based on a polar backbone with C24-26 side chains with alternating ester and carboxylic acid groups.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the oil-soluble high carbon polar modified polymer(s) represent from about 1% to about 20% of the total weight of the composition, more preferably from about 3% to about 17% of the total weight of the composition, and most preferably from about 5% to about 15%, including all ranges and subranges therebetween.

Tackifiers

According to the present invention, compositions comprising at least one tackifier are provided. In accordance with the present invention, a substance is described as a tackifier if, by adding it to a block copolymer, the resulting composition has the properties of a pressure sensitive adhesive. In general, tackifiers can be divided into four different families in terms of their chemistry: hydrocarbon resins, terpenes, amorphous (i.e. non-crystalline) rosins, rosin esters and their derivatives, and pure monomer resins. These tackifiers are characterized by their compatibility with at least one segment of the block copolymer. By the term "compatible", it is meant, for example, that when the block copolymer and tackifier are mixed, the combination of at least one segment of the block copolymer with the tackifier forms a polymer blend having a single glass transition temperature $T_g$ which may be measured by DMA, DSC or neutron light scattering.

The compatibility of the block copolymer and the tackifier may also be defined in terms of solubility parameters. The solubility parameter δ according to the Hansen solubility space is defined in the article *"Solubility Parameter Values"* by Eric A. Grulke in the work *"Polymer Handbook"* 3$^{rd}$ edition, Chapter VII, pages 519-559, the entire content of which is hereby incorporated by reference, by the relationship:

$$\delta=(d_D^2+d_P^2+d_H^2)^{1/2}, \text{ in which:}$$

$d_D$ characterizes the London dispersion forces resulting from the formation of dipoles induced during molecular impacts, $d_P$ characterizes the forces of Debye interactions between permanent dipoles, $d_H$ characterizes the forces of specific interactions (hydrogen bond, acid/base or donor/acceptor type and the like). The definition of the solvents in the three-dimensional solubility space according to Hansen is given in the article by C. M. Hansen: *"The three-dimensional solubility parameters"* J. Paint Technol., 39, 105 (1967), the entire content of which is hereby incorporated by reference.

The at least one tackifier used in the present invention preferably has a solubility parameter corresponding to 6 and the block copolymer preferably has at least one segment whose solubility parameter corresponds to δ±2, preferably δ±1.7, more preferably δ±1.5, more preferably δ±1.3, more preferably δ±1.0, more preferably δ±0.7, more preferably δ±0.5, and more preferably δ±0.3.

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar, where "non-polar" means that the tackifier is substantially free of monomers having polar groups. Preferably, polar groups are not present; however, if they are present, they are preferably present in an amount of up to about 5% by weight, preferably up to about 2% by weight, and more preferably up to about 0.5% by weight.

In preferred embodiments, the tackifier may have a softening point (Ring and Ball, as measured by ASTM E-28) of about 80° C. to about 150° C., preferably about 100° C. to about 130° C. In other preferred embodiments, the tackifier may be liquid and have an R and B softening point of between about −70° C. and about 70° C.

According to preferred embodiments, the tackifiers are hydrogenated hydrocarbon resins such as a hydrogenated styrene/methyl styrene/indene copolymer e.g., styrene/methyl styrene/indene copolymers which include R1090, R1100, R7100, S1100, and S5100, all which are commercially available from Eastman Chemical under the trade name Regalite®. In other embodiments, aliphatic or aromatic hydrocarbon-based tackifying resins, for instance the resins sold under the name "Piccotac" and "Hercotac" from Hercules or "Escorez" from Exxon, may also be used. It is also to be understood that mixtures of tackifiers may also be employed without departing from the spirit of the invention.

A particularly preferred tackifier for use in the present invention is a hydrogenated hydrocarbon resin such as, for example, a hydrogenated styrene/methyl styrene/indene copolymer, commercially available from Eastman under the tradename Regalite® R1100.

In the composition of the present invention, the tackifier(s) are preferably present in an amount of from about 0.1 to about 10 percent by weight, more preferably from 1 to 10 percent by weight, more preferably from 1 to 8 percent by weight and most preferably from 1 to 5 percent by weight of the total weight of the composition, including all ranges and subranges therebetween Block Copolymer According to preferred embodiments of the present invention, compositions further comprising at least one block copolymer are provided. The block copolymers of the present invention are characterized by the presence of at least one "hard" segment, and at least one "soft" segment. Aside from their compositional nature, the hard and soft segments of the block copolymers of the present invention are defined in terms of their respective glass transition temperatures, "$T_g$". More particularly, the hard segment has a $T_g$ of about 50° C. or more, whereas the soft segment has a $T_g$ of about 20° C. or less. The glass transition temperature $T_g$ for the hard block can range from about 50° C. to about 150° C.; about 60° C. to about 125° C.; about 70° C. to about 120° C.; or about 80° C. to about 110° C. The glass transition temperature $T_g$ for the soft segment of the block copolymer can range from about 20° C. to about −150° C.; about 0° C. to about −135° C.; about −10° C. to about −125° C.; and about −25° C. to about −100° C. A more in depth explanation can be found in U.S. Pat. Nos. 5,294,438 and 6,403,070, the entire contents of which are hereby incorporated by reference.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

The amounts of the block (co)polymer or (co)polymers, as well as their structure (di-block, tri-block, etc.), affect the nature of the thermoplastic elastomer, including its gelled form, which may range from fragile to soft/flexible to firm. For instance, soft gels contain relatively high amounts of soft segments, and firm gels contain relatively high amounts of hard segments. The overall properties of the composition may also be affected by including more than one such block copolymer e.g., including a mixture of copolymers. For example, the presence of tri-block copolymers enhances the integrity of the film formed. The gel may also be transparent, translucent or opaque, depending upon the other cosmetically acceptable ingredients added, as described herein.

It is preferred that the styrene content of the block copolymer be less than 30% by weight, preferably less than 25% by weight, and more preferably less than 20% by weight, based on the weight of the block copolymer. This is because of the tendency of block copolymers having a styrene content of greater than 30% by weight to harden/gel in conventional carrier systems. However, in the event that a block copolymer having a styrene content of greater than 30% by weight is used, it may be necessary to also employ a co-solvent or functional ingredient capable of dissolving a styrene block in an amount effective to control the hardening/gelling of the styrene-containing elastomer in the cosmetic composition.

A particularly preferred block copolymer for use in the present invention is a combination of di-block and tri-block copolymers of styrene-ethylene/butylene-styrene, commercially available from Shell Chemical Company under trade name Kraton G1657M. It should be noted, however, that any thermoplastic elastomer of the block copolymer type having at least one soft and at least one hard segment may be used without departing from the spirit of the invention.

The block copolymer will preferably have a solubility parameter, relative to the tackifier component, of $\delta \pm 2$, more preferably $\delta \pm 1.7$, more preferably $\delta \pm 1.5$, more preferably $\delta \pm 1.3$, more preferably $\delta \pm 1.0$, more preferably $\delta \pm 0.7$, more preferably $\delta \pm 0.5$, and more preferably $\delta \pm 0.3$.

In the composition of the present invention, the block copolymer(s) are preferably present in an amount of from about 1 to about 10 percent by weight, more preferably from 1 to 8 percent by weight, more preferably from 1 to 6 percent by weight and most preferably from 1 to 5 percent by weight of the total weight of the composition, including all ranges and subranges therebetween.

According to particularly preferred embodiments, the compositions of the present invention comprise an equivalent amount of the at least one block copolymer and the at least one tackifier, or more of the at least one block copolymer as compared to the at least one tackifier. For example, the at least one block copolymer and the at least one tackifier can be present in ratios of 1.25, 1.00, 0.75, 0.50, 0.33, 0.25, and 0.10, including all ranges and subranges therebetween, with ratios from 1.00 to 0.33 being particularly preferred.

Also preferably, the ratio of polar modified polymer to block copolymer/tackifier ranges from about 10:1 to about 1:10, more preferably from about 1:5 to about 5:1, and most preferably from about 1:3 to about 3:1.

According to a particularly preferred embodiment of the present invention, compositions comprising block copolymer, tackifier and polar modified polymer possess synergistically improved properties with respect to lengthening, lifting or holding keratin materials such as hair or eyelashes. That is, surprisingly, the combination of block copolymer, tackifier and polar modified polymer results in increased ability to hold, lift or lengthen keratin materials such as hair or eyelashes in an amount which is more than additive.

Alkyl Silsesquioxane Resin

According to preferred embodiments of the present invention, compositions further comprising at least one alkyl silsesquioxane resin are provided. Alkyl silsesquioxane resins are silsesquioxane homopolymers and/or copolymers having an average siloxane unit of the general formula $R^1{}_n SiO_{(4-n)/2}$, wherein each $R^1$ is independently chosen from a hydrogen atom and a $C_1$-$C_{10}$ alkyl group, wherein more than 80 mole % of $R^1$ represent a $C_3$-$C_{10}$ alkyl group, n is a value of from 1.0 to 1.4, and more than 60 mole % of the copolymer comprises $R^1 SiO_{3/2}$ units.

Preferably, the silsesquioxane resin used is one where $R^1$ is a $C_1$-$C_{10}$, preferably a $C_1$-$C_4$ alkyl group, and more preferably a propyl group. Examples of alkyl silsesquioxane resins suitable for use in the present invention are propyl silsesquioxane resins. One such propyl silsesquioxane resin is commercially available from Dow-Corning as Dow Corning® 670 Fluid.

The alkyl silsesquioxane resin is preferably present in the cosmetic composition of the present invention in an amount ranging from about 3% to about 50% by weight, such as from about 5% to about 30% by weight, based on the weight of the composition, including all ranges and subranges therebetween.

Solvents

According to preferred embodiments, the compositions of the present invention further comprise at least one solvent capable of solubilizing the hard or soft segment of the block copolymer. Such suitable solvents are typically characterized in terms of their viscosity at room temperature, weight average molecular weight and/or solubility parameter in relation to the at least one hard segment of the block copolymer.

Solvent(s) capable of solubilizing the hard segment of the block copolymer will preferably have a viscosity, at room temperature, of from about 1 to about 200 cps, more preferably from 1 to 150 cps, more preferably from 1 to 100 cps, more preferably from 2 to 60 cps, and more preferably from 2 to 40 cps.

Solvent(s) capable of solubilizing the hard segment of the block copolymer used in the present invention will preferably have a solubility parameter corresponding to $\delta'$ and the block copolymer will preferably have at least one hard segment whose solubility parameter corresponds to $\delta' \pm 2$, more preferably $\delta' \pm 1.7$, more preferably $\delta' \pm 1.5$, more preferably $\delta' \pm 1.3$, more preferably $\delta' \pm 1.0$, more preferably $\delta' \pm 0.7$, more preferably $\delta' \pm 0.5$, and more preferably $\delta' \pm 0.3$.

Examples of nonvolatile solvents capable of solubilizing the hard segment of the block copolymer which can be used in the invention include, but are not limited to, monoesters, diesters, triesters, mixed aliphatic and/or aromatic, polar oils such as: hydrocarbon-based oils of animal origin, such as perhydrosqualene; hydrocarbon-based plant oils such as liquid triglycerides of fatty acids and of glycerol, in which the fatty acids may have varied chain lengths, these chains being linear or branched, and saturated or unsaturated; these oils can be chosen, for example, from wheat germ oil, sunflower oil, corn oil, soybean oil, marrow oil, grapeseed oil, blackcurrant seed oil, sesame oil, hazelnut oil, apricot oil, macadamia oil, castor oil, avocado oil, karite butter, sweet almond oil, cotton oil, alfalfa oil, poppy oil, pumpkin oil, evening primrose oil, millet oil, barley oil, quinoa oil, olive oil, rye oil, safflower oil, candlenut oil, passion flower oil, musk rose oil and caprylic/capric acid triglycerides such as those sold by the company Stéarineries Dubois or those sold under the names Miglyol 810, 812 and 818 by the company Dynamit Nobel; natural or synthetic esters of formula $R_1 COOR_2$, wherein $R_1$ is a higher fatty acid residue comprising 7 to 19 carbon atoms, and $R_2$ is a branched hydrocarbon-based chain comprising 3 to 20 carbon atoms, such as, for example, purcellin oil (cetostearyl octanoate), isopropyl myristate and alkyl or polyalkyl octanoates, decanoates or ricinoleates; synthetic ethers of formula $R^3 COR^4$, wherein $R^3$ is a $C_3$ to $C_{19}$ alkyl radical, and $R^4$ is a $C_3$ to $O_{20}$ alkyl radical; fatty alcohols comprising at least 12 carbon atoms, such as octyldodecanol or oleyl alcohol; cyclic hydrocarbons such as (alkyl)cycloalkanes, wherein the alkyl chain is linear or branched, saturated or unsaturated and comprises 1 to 30 carbon atoms, such as cyclohexane or dioctylcyclohexane; aromatic hydrocarbons, for example, alkenes such as benzene, toluene, 2,4-dimethyl-3-cyclohexene, dipentene, p-cymene, naphthalene or anthracene, and esters such as isostearyl benzoate; primary, secondary or tertiary amines such as triethanolamine; and mixtures thereof. In one embodiment, synthetic esters such as isopropyl myristate are used.

Preferred esters are those having a weight average molecular weight (Mw) in the range of about 100 to about 600, preferably from 100 to 500. Examples thereof include, but are not limited to, C12-15 alkyl benzoate, isopropyl myristate (Mw=270), isopropyl palmitate (Mw=300), isononyl isononanoate, cetyl ethylhexanoate (Mw=368), neopentyl glycol diethylhexanoate (Mw=356), diisopropyl sebacate (Mw=286).

Solvent(s) capable of solubilizing the hard segment of the block copolymer, if present, may typically be present in the composition of the invention in an amount of up to about 85% by weight; up to 75% by weight; up to 55% by weight; up to 45% by weight; up to 40% by weight; up to 30% by weight; up to 20% by weight; up to 10% by weight; and up to 5% by weight, based on the weight of the composition.

Solvents capable of solubilizing the soft segment of the block copolymer which may be used in accordance with preferred embodiments of the present invention are typically characterized in terms of their viscosity at room temperature, weight average molecular weight and/or solubility parameter in relation to the at least one soft segment of the block copolymer.

Solvent(s) capable of solubilizing the soft segment of the block copolymer will preferably have a viscosity, at room temperature, of from about 1 to about 50 cps, more preferably from 1 to 40 cps, more preferably from 1 to 30 cps, more preferably from 2 to 20 cps, and more preferably from 2 to 10 cps.

Solvent(s) capable of solubilizing the soft segment of the block copolymer used in the present invention will preferably have a solubility parameter corresponding to $\delta'$ and the block copolymer will preferably have at least one soft segment whose solubility parameter corresponds to $\delta' \pm 2$, more preferably $\delta' \pm 1.7$, more preferably $\delta' \pm 1.5$, more preferably $\delta' \pm 1.3$, more preferably $\delta' \pm 1.0$, more preferably $\delta' \pm 0.7$, more preferably $\delta' \pm 0.5$, and more preferably $\delta' \pm 0.3$.

Solvent(s) capable of solubilizing the soft segment of the block copolymer may be selected from volatile solvents and nonvolatile solvents. The expression "volatile solvent" means a solvent that is capable of evaporating at room temperature from a support onto which it has been applied, in other words a solvent which has a measurable vapor pressure at room temperature. See, U.S. Pat. No. 6,656,458, the entire content of which is hereby incorporated by reference.

Representative examples of suitable volatile organic solvents include, but are not limited to, volatile hydrocarbon-based oils. The expression "hydrocarbon-based oil" means oil containing only hydrogen and carbon atoms. Examples of volatile hydrocarbon-based oils include isoparaffins, i.e., branched alkanes containing from 8 to 16 carbon atoms, and in particular isododecane (also known as 2,2,4,4,6-pentamethylheptane). It is also possible to use mixtures of such isoparaffins. Other volatile hydrocarbon-based oils, such as petroleum distillates, can also be used.

Representative examples of suitable volatile silicone solvents include, but are not limited to, linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Suitable nonvolatile solvents which can be used are those having a weight average molecular weight in the range of about 150 to about 450, preferably from 200 to 350. Examples thereof include, but are not limited to, hydrogenated polydecene, hydrogenated polyisobutene, isoeicosane, polydecene and polybutene.

Solvent(s) capable of solubilizing the soft segment of the block copolymer, if present, may typically be present in the composition of the invention in an amount of up to about 85% by weight; up to 75% by weight; up to 55% by weight; up to 45% by weight; up to 40% by weight; up to 30% by weight; up to 20% by weight; up to 10% by weight; and up to 5% by weight, based on the weight of the composition.

According to preferred embodiments of the present invention, at least one co-solvent having a high molecular weight and high viscosity may also be used in the invention compositions.

Examples of suitable high viscosity co-solvents which are compatible with the hard segment of the block copolymer include, but are not limited to, capric/caprylic triglyceride (Mw=500), diisopropyl dimer dilinoleate (Mw=644), diisostearyl fumarate (Mw=620), diisostearyl malate (Mw=640), pentaerythrityl tetraoleate, neopentyl glycol diethylhexanoate, diethylhexyl sebacate and tricaprylate/tricaprate. The weight average molecular weight of these co-solvents is preferably from about 500 to about 1000, and more preferably from 500 to 800.

Examples of suitable high viscosity co-solvents which are compatible with the soft segment of the block copolymer include, but are not limited to, polyisobutene, hydrogenated polyisobutene, polybutene, hydrogenated polybutene, polydecene and hydrogenated polydecene. The weight average molecular weight of these co-solvents is preferably from about 2,500 to about 100,000, and more preferably from 3,000 to 10,000.

These co-solvents, if present, may preferably be employed in the composition of the invention in an amount of up to about 50% by weight; up to 40% by weight; up to 30% by weight; up to 25% by weight; all weights based on the weight of the composition.

Viscosity Increasing Agents

The composition may also contain elastomeric compounds such as those sold or made under the names KSG6 from Shin-Etsu, Trefil E-505C or Trefil E-506C from Dow-Corning, Gransil from Grant Industries (SR-CYC, SR DMF10, SR-DC556) or those marketed in the form of preconstituted gels (KSG15, KSG17, KSG16, KSG18, KSG21 from Shin-Etsu, Gransil SR 5CYC gel, Gransil SR DMF 10 gel, Gransil SR DC556 gel, SF 1204 and JK 113 from General Electric or emulsifying elastomers such as those sold under the names of KSG-210, KSG-30, KSG-31, KSG-32, KSG-33, KSG-40, KSG 41, KSG-42, KSG-43 and KSG-44 from Shin-Etsu.

The composition may also contain modified clays such as, for example, hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as steralkonium bentonites, such as the products sold or made under the names Claytone APA and Claytone AF by the company Southern Clay, and Baragel 24 sold or made by the company Rheox.

The composition may also contain silica, such as fumed silica. The fumed silica may have a particle size, which may be nanometric to micrometric, for example ranging from about 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-55®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be (a) trimethylsiloxyl groups, which are obtained in particular by treating fumed silica in the presence of hexamethyldisilazane. Silicas thus treated are known as "silica silylate" according to the CTFA (6th edition, 1995). They are sold or made, for example, under the references "Aerosil R812®" by the company Degussa and "CAB-O-SIL TS-530®" by the company Cabot; (b) dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold or made, for example, under the references "Aerosil R972®" and "Aerosil R974®" by the company Degussa, and "CAB-O-SIL TS-6100" and "CAB-O-SIL TS-720®" by the company Cabot; and (c) groups derived from reacting fumed silica with silane alkoxides or siloxanes. These treated silicas are, for example, the products sold or made under the reference "Aerosil R805®" by the company Degussa.

Using hydrophobic silicas, such as fumed silica, makes can help in obtaining a translucent or even transparent composition, in particular in the form of a stick, which does not exude, in the absence of opacifying particles such as waxes, fillers and pigments (including nacres).

The composition may also contain at least one typical wax. For the purposes of the present invention, a typical wax is a lipophilic fatty compound that is solid at room temperature (25° C.) and atmospheric pressure (760 mmHg, i.e. 101 KPa), which undergoes a reversible solid/liquid change of state, having a melting point of greater than 40° C. and further such as greater than 55° C. and which may be up to 200° C. By bringing the wax to its melting point, it is possible to make it miscible with oils and to form a microscopically homogeneous mixture, but on returning the temperature of the mixture to room temperature, recrystallization of the wax in the oils of the mixture is obtained. It is this recrystallization in the mixture which is responsible for the reduction in the gloss of the mixture.

For the purposes of the invention, the waxes are those generally used in cosmetics and dermatology; they are, for example, of natural origin, for instance beeswax, ozokerite, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil as well as waxes of synthetic origin, for instance polyethylene waxes derived from the polymerization of ethylene, waxes obtained by Fischer-Tropsch synthesis, fatty acid esters and glycerides that are solid at 40° C., for example, at above 55° C., fatty alcohol waxes such as those sold by Baker Petrolite under the Performacol name (Performacol 350, 425 and 550) including C30-050 alcohols, silicone waxes such as alkyl- and alkoxy-poly(di)methylsiloxanes and/or poly(di)methyl-siloxane esters that are solid at 40° C., for example, at above 55° C.

According to the invention, the melting point values correspond to the melting peak measured by the "Differential Scanning Calorimetry" method with a temperature rise of 5 or 10° C./min.

The composition may also include polysilicone-polyamide copolymers such as those disclosed in U.S. patent application publication no. 2004/0170586, and/or a rheological modifying polymer such as PVP.

However, according to particularly preferred embodiments, the compositions contain so little of the viscosity increasing agents discuss above that the presence of such agents does not affect the cosmetic properties of the composition. Preferably, the compositions are substantially free of such viscosity increasing agents (i.e., contain less than about 1% viscosity increasing agents), essentially free of such viscosity increasing agents (i.e., contain less than about 0.5% viscosity increasing agents) or free of such viscosity increasing agents (i.e., contain less than about 0.1% viscosity increasing agents).

According to particularly preferred embodiments, the compositions contain so little elastomer and/or wax that the presence of such elastomers and/or waxes does not affect the cosmetic properties of the composition. Preferably, the compositions are substantially free of such elastomers and/or waxes (i.e., contain less than about 0.5% elastomers and/or waxes), essentially free of such elastomers and/or waxes (i.e., contain less than about 0.25% elastomers and/or waxes) or free of such elastomers and/or waxes (i.e., contain less than about 0.1% elastomers and/or waxes).

Coloring Agents

According to the present invention, the compositions may optionally comprise at least one coloring agent (colorant). Suitable coloring agents include but are not limited to pigments, dyes, such as liposoluble dyes, nacreous pigments, and pearling agents. Typically, when the composition contains colorants, it is a make-up composition such as a mascara composition. Alternatively, when the composition does not contain colorants, it is a clear or transparent composition which can be used as a basecoat (or topcoat) prior to (or after) application of a make-up composition such as a mascara to eyelashes, or it can be used as a hair treatment composition such as, for example, a hair conditioner or mousse. However, it is possible that topcoats, basecoats, hair treatment products and the like could contain colorants, and/or that a mascara or make-up composition could contain little or no colorant.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%. In the case of certain products, the pigments, including nacreous pigments, may, for example, represent up to 50% by weight of the composition.

Film Forming Agents

According to particularly preferred embodiments of the present invention, compositions optionally further comprising at least one at least one film forming agent (film former) are provided. Acceptable film forming agents are known in the art and include, but are not limited to, those disclosed in U.S. patent application publication no. 2004/0170586, the entire contents of which is hereby incorporated by reference. Non-limiting representative examples of such film forming agents include other silicone resins such as, for example, MQ resins (for example, trimethylsiloxysilicates), and MK resins (for example, polymethylsilsesquioxanes), silicone esters such as those disclosed in U.S. Pat. Nos. 6,045,782, 5,334, 737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981, 903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

According to preferred embodiments, the film former, when present, is present in the composition in an amount ranging from 0.1% to 30% by weight relative to the total weight of the composition. Preferably, the film former is present in an amount ranging from 0.5% to 20% by weight relative to the total weight of the composition, and more preferably from 2% to 15%, including all ranges and subranges therebetween. One of ordinary skill in the art will recognize that the film former of the present invention may be commercially available, and may come from suppliers in the form of a dilute solution. The amounts of the film former disclosed herein therefore reflect the weight percent of active material.

According to preferred embodiments of the present invention, the compositions of the present invention are anhydrous. By "anhydrous," it is meant that the composition contains substantially no water (that is, less than about 0.5% by weight of the composition of water).

According to other preferred embodiments, the compositions of the present invention further comprise water. In this embodiment, water is preferably present in an amount ranging from about 0.6 to about 70%, preferably from about 3.0 to 60%, and more preferably from about 5 to about 50% relative to the total weight of the composition. Preferably, such water-containing cosmetic compositions are emulsions or dispersions.

According to particularly preferred embodiments, the compositions of the present invention are in the form of an emulsion. Suitable emulsion forms include but are not limited to oil-in-water, water-in-oil, oil-in-water-in-oil, water-in-oil-in-water and nanoemulsions (emulsions whose oil globules are of very fine particle size, that is to say that they have a number-average size of less than about 100 nanometers (nm)). Emulsions contain at least one oil phase and at least one aqueous phase. Typically speaking, emulsions contain surfactants or surfactant-like materials which provide stability to the emulsions and inhibit de-phasing of the emulsions.

Additional Additives

The composition of the invention can also comprise any additive usually used in the field under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, pasty compounds and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* (9th ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

Non-limiting examples of such additional components include non-volatile oils such as silicone oils (for example, dimethicone, phenyl trimethicone, trimethyl pentaphenyl trisiloxane, etc) or hydrocarbon oils (for example, esters). In one embodiment of the present invention, the compositions of the present invention are substantially free of silicone oils (i.e., contain less than about 0.5% silicone oils). In another embodiment, the compositions are substantially free of non-silicone oils (i.e., contain less than about 0.5% non-silicone oils). In another embodiment, the compositions are substantially free of non-volatile oils (i.e., contain less than about 0.5% non-volatile oils).

According to preferred embodiments of the present invention, methods of increasing keratin material (for example, hair or eyelash) lift, hold and/or length comprising applying to keratin materials a keratin material lift-, hold- and/or length-increasing effective amount of a composition comprising at least one polar modified polymer and at least one tackifier, and optionally at least one block copolymer and/or at least one alkyl silsesquioxane resin are provided. The compositions may be applied to the keratin materials as needed, preferably once or twice daily, more preferably once daily and then preferably allowed to dry before subjecting to contact such as with clothing or other objects.

According to particularly preferred embodiments, sufficient polar modified polymer is combined with sufficient tackifier, and optionally sufficient block copolymer and/or alkyl silsesquioxane resin, such that the performance properties of the compositions are greater than the performance properties of compositions containing either ingredient individually (that is, synergism exists with respect to the at least one polar modified polymer, at least one tackifier, at least one block copolymer and/or at least one alkyl silsesquioxane resin). According to yet other preferred embodiments, the combination of such elements does not result in a significant reduction in gloss or shine of the composition, and/or poor texture or tackiness properties upon application of the composition, yet provides sufficient gelling to the composition.

According to yet further embodiments of the present invention, methods of making-up keratin materials (for example, hair or eyelashes) comprising applying a keratin material making-up effective amount of a composition comprising at least one polar modified polymer and at least one tackifier, and optionally at least one block copolymer and/or at least one alkyl silsesquioxane resin to keratin materials in need of such making-up are provided. Preferably, "making up" the keratin material includes applying at least one coloring agent to the keratin material in an amount sufficient to provide color to the keratin material.

According to preferred embodiments of the present invention, methods of treating or caring for keratin materials (for example, hair or eyelashes) by applying compositions of the present invention to the keratin materials in an amount sufficient to treat and/or care for the keratin materials are provided.

According to other preferred embodiments, methods of enhancing the appearance of keratin materials (for example, hair or eyelashes) by applying compositions of the present invention to the keratin materials in an amount sufficient to enhance the appearance of the keratin materials are provided.

In accordance with the preceding preferred embodiments, the compositions of the present invention are applied topically to keratin materials (for example, hair or eyelashes) in an amount sufficient to treat, care for and/or make up the keratin materials, or to enhance the appearance of the keratin materials. The compositions may be applied to eyelashes as needed, preferably once or twice daily, more preferably once daily and then preferably allowed to dry before subjecting to contact such as with clothing or other objects. According to yet other preferred embodiments, the combination of such elements does not result in a significant reduction in gloss or shine of the composition, and/or poor texture or tackiness properties upon application of the composition (that is, the composition glides on well without significant drag), yet provides sufficient gelling to the composition.

According to yet other embodiments of the present invention, methods of making a composition comprising mixing together at least one polar modified polymer and at least one tackifier, and optionally at least one block copolymer and/or at least one alkyl silsesquioxane resin to form a composition are provided. In particularly preferred embodiments, the polar modified polymer is in an aqueous phase, and the tackifier, block copolymer and/or alkyl silsesquioxane resin are in an oil phase, and the tackifier, block copolymer and/or alkyl silsesquioxane resin and polar modified polymer are combined when the aqueous phase and the oil phase are combined. Such preferred procedures allow, among other things, the preparation of emulsions which are substantially or essentially free of surfactants.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Examples 1 & 2

Mascara

| Phase | INCI Name/Trade Name | EX1 | EX2 |
|---|---|---|---|
| A1 | DI Water | 52.06 | 51.21 |
| | Amphisol K | 1.73 | 1.73 |
| | Eastman AQ | 0.75 | 0.75 |
| | PVP K90 | 1.00 | 1.00 |
| | Flexan II | 0.70 | 0.70 |
| | Methylparaben | 0.25 | 0.25 |
| | Hydroxypropylcelulose | 0.02 | 0.02 |
| | Pentylene Glycol | 2.00 | 2.00 |
| | Di Sodium EDTA | 0.10 | 0.10 |
| A2 | Resyn 28 | 1.00 | 1.00 |
| | Amphomer LV 71 | 1.00 | 1.00 |
| | AMP | 0.05 | 0.05 |

-continued

| Phase | INCI Name/Trade Name | EX1 | EX2 |
|---|---|---|---|
| A3 | Simethicone | 0.15 | 0.15 |
| B | Steareth-2 | 2.10 | 2.10 |
| | Steareth-20 | 4.44 | 4.44 |
| | Cetyl Alcohol | 2.00 | 2.00 |
| | Carnuaba Wax | 3.00 | 2.00 |
| | Candellia Wax | 3.00 | 2.00 |
| | Rice Bran Wax | 4.00 | 2.50 |
| | Licocare PP207 LP3349 | 5.65 | 10.00 |
| | Propylparaben | 0.20 | 0.20 |
| | Sunpuro Black | 5.00 | 5.00 |
| C | Isododecane | 5.00 | 5.00 |
| | Hydrocarbon Resin | 2.00 | 2.00 |
| | Kraton G1657M | 1.00 | 1.00 |
| D | Fixate G100 | 0.70 | 0.70 |
| E | Liquapar Optima | 1.10 | 1.10 |
| | | 100.00 | 100.00 |
| | AVERAGE % LENGTHENING EFFECT | 31.9% | 43.1% |

Example 3 & 4

Lip Gloss

| Seq | Trade Name | INCI Name | EX3 | EX4 |
|---|---|---|---|---|
| A | Kraton polymer G1657 m | Polystyrene/Polyethylene-butylene/Polystyrene | 8.00 | 8.00 |
| | Regalite R1100 | hydrogenated styrene/methyl styrene/indiene | 16.00 | 16.00 |
| | polysylane lite | Polyisobutene | 33.20 | 33.20 |
| B | Iso propyl palmitate | Iso propyl palmitate | 6.00 | 6.00 |
| | DC556 | phenyl trimethicone | 9.80 | 9.80 |
| | DC 555 | trimethyl pentaphenyl trisiloxane | 10.00 | 10.00 |
| | PURESYN6 | Polydecene | 8.00 | 8.00 |
| | PURESYN150 | Polydecene | 6.00 | 6.00 |
| C | fumed silica | fumed silica | 3.00 | 0.00 |
| | LicoCare PP 207 LP3349 | poly propylene-Maleic Anhydride wax | 0.00 | 3.00 |
| | | total= | 100.00 | 100.00 |

Example 4 containing polar modified polymer (LicoCare), a tackifier (Regalite) and a block copolymer (Kraton) produced a lip gloss which was shinier yet clearer than the Example 3 lip gloss containing silica. Moreover, the lip gloss of example 4 addressed the problem of bubble entrapment, which accompanies the use of silica. Finally, the lip gloss of example 4 had better application properties than the lip gloss of example 3. In particular, the lip gloss of example 4 had a pleasant, non-sticky sensation upon application.

Inventive Foundations

Examples 5 and 6

| | | Ex. 5 | Ex. 6 |
|---|---|---|---|
| A1 | Isododecane | 33.0 | 33.0 |
| | LICOCARE PP207 LP1332 | 4.0 | 0.0 |
| | LICOCARE CM401 LP3345 | 0.0 | 4.0 |
| | Polyethylene 400 Wax | 0.0 | 0.0 |
| | Hydrogenated styrene/methyl styrene/indene copolymer Regalite | 10.0 | 10.0 |
| | T-Propyl silsesquioxane | 2.6 | 2.6 |

-continued

|    |                                                                  | Ex. 5 | Ex. 6 |
|----|------------------------------------------------------------------|-------|-------|
| A2 | Disteardimonium Hectorite                                        | 1.2   | 1.2   |
|    | Acrylate copolymer                                               | 0.2   | 0.2   |
| A3 | PEG-9 Polydimethylsiloxyethyl dimethicone and PEG-9              | 2.5   | 2.5   |
|    | Pigment Grind 4323-143                                           | 11.5  | 11.5  |
|    | Dimethicone and Dimethicone/Polyglycerin-3 Crosspolymer          | 4.0   | 4.0   |
| A4 | Nylon-12                                                         | 1.5   | 1.5   |
| B  | Sodium Chloride                                                  | 1.0   | 1.0   |
|    | Disodium EDTA                                                    | 0.2   | 0.2   |
|    | Glycerin                                                         | 3.0   | 3.0   |
|    | Preservatives                                                    | 0.8   | 0.8   |
|    | DI water                                                         | 24.5  | 24.5  |
|    | TOTAL                                                            | 100.0 | 100.0 |

Comparative Foundation

Example A

|    |                                                                  | Ex. A |
|----|------------------------------------------------------------------|-------|
| A1 | Isododecane                                                      | 33.0  |
|    | LICOCARE PP207 LP1332                                            | 0.0   |
|    | LICOCARE CM401 LP3345                                            | 0.0   |
|    | Polyethylene 400 Wax                                             | 4.0   |
|    | Hydrogenated Styrene/Methyl Styrene/Indene (Regalite R1100)      | 10.0  |
|    | T-Propyl Silsesquioxane (75% in isododecane)                     | 2.6   |
| A2 | Disteardimonium Hectorite                                        | 1.2   |
|    | Acrylate Copolymer                                               | 0.2   |
| A3 | PEG-9 Polydimethylsiloxyethyl Dimethicone and PEG-9              | 2.5   |
|    | Pigment Grind 4323-143                                           | 11.5  |
|    | Dimethicone and Dimethicone/Polyglycerin-3 Crosspolymer          | 4.0   |
| A4 | Nylon-12                                                         | 1.5   |
| B  | Sodium Chloride                                                  | 1.0   |
|    | Disodium EDTA                                                    | 0.2   |
|    | Glycerin                                                         | 3.0   |
|    | Preservatives                                                    | 0.8   |
|    | DI water                                                         | 24.5  |
|    | TOTAL                                                            | 100.0 |

Inventive Foundations

Examples 7 and 8

|    |                                                                  | Example 7 | Example 8 |
|----|------------------------------------------------------------------|-----------|-----------|
| A1 | Isododecane                                                      | 31.0      | 19.0      |
|    | LICOCARE PP207 LP1332                                            | 6.0       | 0.0       |
|    | LICOCARE CM401 LP3345                                            | 0.0       | 18.0      |
|    | Polyethylene 400 Wax                                             | 0.0       | 0.0       |
|    | Hydrogenated styrene/methyl styrene/indene copolymer Regalite    | 10.0      | 10.0      |
|    | T-Propyl silsesquioxane                                          | 2.6       | 2.6       |
| A2 | Disteardimonium Hectorite                                        | 1.2       | 1.2       |
|    | Acrylate Copolymer                                               | 0.2       | 0.2       |
| A3 | PEG-9 Polydimethylsiloxyethyl Dimethicone and PEG-9              | 2.5       | 2.5       |
|    | Pigment Grind 4323-143                                           | 11.5      | 11.5      |
|    | Dimethicone and Dimethicone/Polyglycerin-3 Crosspolymer          | 4.0       | 4.0       |

|    |                | Example 7 | Example 8 |
|----|----------------|-----------|-----------|
| A4 | Nylon-12       | 1.5       | 1.5       |
| B  | Sodium Chloride| 1.0       | 1.0       |
|    | Disodium EDTA  | 0.2       | 0.2       |
|    | Glycerin       | 3.0       | 3.0       |
|    | Preservatives  | 0.8       | 0.8       |
|    | DI water       | 24.5      | 24.5      |
|    | TOTAL          | 100.0     | 100.0     |

Pigment Grind

| Titanium Dioxide | Titanium Dioxide (and) Disodium Stearoyl Glutamate (and) Aluminum Hydroxide | 7.175 |
|---|---|---|
| Iron Oxide-Yellow | Iron Oxides (and) Disodium Stearoyl Glutamate (and) Aluminum Hydroxide | 1.890 |
| Iron Oxide-Red | Iron Oxides (and) Disodium Stearoyl Glutamate (and) Aluminum Hydroxide | 0.730 |
| Iron Oxide-Black | Iron Oxides (and) Disodium Stearoyl Glutamate (and) Aluminum Hydroxide | 0.203 |
| D5 | Cyclopentasiloxane | 4.000 |

It was found that the use of polar modified polymers improved the wear and the comfort.

Procedure

Add phase A1 under high speed mixer—heat until fully dissolved (should not exceed 80° C.)—cover beaker.

Add phase A2 until fully dissolved. Maintain heat.

Add phase A3 followed by phase A4. Use high sheer—10 minutes until fully mixed.

Heat phase B in separate beaker until fully dissolved. Match temperature to phase A (~65° C.).

When both phase A and B are fully mixed and at the same temperature, add phase B slowly to phase A at high sheer.

Mix emulsion for ~15 minutes. Cool.

Mascara Inventive Example 9

|                                              | Ex. 9  |
|----------------------------------------------|--------|
| Isododecane                                  | 30.56  |
| LICOCARE PP207 LP3349                        | 11.64  |
| T-Propyl Silsesquioxane (75% in isododecane) | 20.20  |
| Regalite 1100                                | 28.20  |
| Sunpuro Black Iron Oxide                     | 9.40   |
| TOTAL                                        | 100.00 |

It was found that the use of a single wax, the polar modified polymer, contributes to volume, intense color, wear and a creamy texture in this mascara.

Procedure

In the main kettle begin heating Isododecane to 65-75° C. Under mixing, add LICOCARE PP207 LP3349, mix, add Regalite 1100 and dissolve under vigorous mixing (about 15 minutes)

After the solid is completely dissolved add T-Propyl silsesquioxane and mix until dissolved.

When well mixed, transfer to homogenizer, add Sunpuro Black Iron Oxide and homogenize for at least 1 hour.

When everything is uniform transfer to paddle mixer.

When cool, drop the batch.

Examples 10-12

| | Trade Name | INCI Name | Example 10 | Example 11 | Example 12 |
|---|---|---|---|---|---|
| A1 | Iso | isododecane | 35.6 | 35.6 | 35.6 |
| A1 | PP207 | PP207 Metallocene Wax | 0 | 4 | 0 |
| | CM401 | CM401 Metallocene Wax | 0 | 0 | 4 |
| | PE400 | Polyethylene 400 Wax | 4 | 0 | 0 |
| A1 | Regalite | HYDROGENATED STYRENE/METHYL STYRENE/INDENE COPOLYMER | 10 | 10 | 10 |
| | dc xx-5002 | t propyl in iso | 0 | 0 | 0 |
| A2 | Bentone | DISTEARDIMONIUM HECTORITE | 1.2 | 1.2 | 1.2 |
| | | acrylate coplymer | 0.2 | 0.2 | 0.2 |
| A3 | KF-6028 | PEG-9 POLYDIMETHYL-SILOXYETHYL DIMETHICONE (and) PEG-9 | 2.5 | 2.5 | 2.5 |
| A3 | | pigmentgrind | 11.5 | 11.5 | 11.5 |
| A3 | KSG 710 | Dimethicone and Dimethicone/ Polyglycerin-3 Crosspolymer | 4 | 4 | 4 |
| A4 | ORGASOL 2002 | Nylon-12 | 1.5 | 1.5 | 1.5 |
| | sodium choloride | sodium chloride | 1 | 1 | 1 |
| | disodium edta | disodium edta | 0.2 | 0.2 | 0.2 |
| B | Glycerin | Glycerin | 3 | 3 | 3 |
| B | PHENONIP | Phenoxyethanol etc. | 0.8 | 0.8 | 0.8 |
| B | DI WATER | DI WATER | 24.5 | 24.5 | 24.5 |
| | | total: | 100 | 100 | 100 |
| | | Performance Characteristics | more transfer less wear | less transfer high wear | less transfer high wear |

Procedure for making examples 10-12:

1. Phase A1 was added under high speed mixer—heated until fully dissolved (should not exceed 80 C)—covered beaker
2. Phase A2 was added until fully dissolved. Maintained heat.
3. Phase A3 was added, followed by phase A4. Used high sheer ~10 minutes until fully mixed
4. Phase B was heated in a separate beaker until fully dissolved. Matched temperature to phase A (~65C)
5. When both phase A and B were fully mixed and at the same temperature, phase B was slowly added to Phase A at High Sheer
6. Mixed emulsion for ~15 minutes. Then allowed to cool.

Lip Composition Inventory Examples 13-15

| | Trade Name | INCI Name | EX 13 | EX 14 | EX 15 |
|---|---|---|---|---|---|
| A | PERMETHYL 99A | Isododecane | 31.33 | 31.33 | 25.33 |
| | Regalite R1100 | Hydrogenated styrene/methyl styrene/indene | 30.00 | 30.00 | 30.00 |
| | | POLYPROPYL-SILSESQUIOXANE (75% solids in isododecane) | 6.67 | 6.67 | 6.67 |
| B | | Black Iron Oxide | 0.40 | 0.40 | 0.40 |
| | | Titanium dioxide | 1.22 | 1.22 | 1.22 |
| | | red/brown iron oxide | 2.52 | 2.52 | 2.52 |
| | | Red #7 | 1.86 | 1.86 | 1.86 |
| | PERMETHYL 99A | Isododecane | 8.00 | 8.00 | 8.00 |
| | Regalite R1100 | Hydrogenated Styrene/Methyl Styrene/Indene | 8.00 | 8.00 | 8.00 |
| C | | Silica | 2.00 | 2.00 | 2.00 |
| | | Mica | 2.00 | 2.00 | 2.00 |
| | LICOCARE CM 401 LP 3345 | C26-28 Alpha Olefin-Maleic anhydride wax | 6.00 | 0.00 | 12.00 |
| | LICOCARE PP 207 LP1332 | Polypropylene-Maleic Anhydride Wax (MW = 6400) | 0.00 | 6.00 | 0.00 |
| | | TOTAL | 100.00 | 100.00 | 100.00 |

Film Properties:

| | Ex. 13 | Ex. 14 | Ex. 15 |
|---|---|---|---|
| gloss at 20° | 31.3 | 46.1 | 16.8 |
| gloss at 60° | 65.6 | 82.7 | 57.3 |
| Wear | | 77 ± 13 | 85 ± 7 |
| Shine | | 157.7 ± 20 | 148 ± 19 |
| Transfer | | 2.5 ± 0.8 | 2 ± 0.8 |

What is claimed is:

1. A composition comprising: (a) at least one polar modified polymer selected from the group consisting of (1) a polar modified polymer consisting essentially of C26-C28 units and modified with at least one maleic anhydride unit, and having a weight-average molecular weight of less than or equal to 30000 g/mol and a crystallinity of 8% to 60%; (2) a polar modified polymer consisting essentially of C2-C4 units and modified with at least one maleic anhydride unit, and having a weight-average molecular weight of less than or equal to 25 000g/mol and a melting point above 75° C., and mixtures thereof; (b) at least one tackifier, wherein the tackifier is a hydrocarbon resin; and (c) at least one block copolymer, wherein the at least one block copolymer comprises styrene and is an A-B polymer or an A-B-A polymer, where A represents a hard segment and B represents a soft segment, wherein the at least one tackifier and the at least one block copolymer form a pressure sensitive adhesive, and wherein the composition does not comprise a plasticizer.

2. The composition of claim 1, wherein the composition is an emulsion.

3. The composition of claim 1, further comprising at least one coloring agent.

4. The composition of claim 1, wherein the at least one polar modified polymer is a wax consisting essentially of polypropylene and maleic anhydride units.

5. The composition of claim 1, wherein the at least one polar modified polymer is a wax consisting essentially of C26-C28 alpha olefin and maleic acid anhydride units.

6. The composition of claim 1, further comprising an alkyl silsesquioxane resin.

7. A method of making up eyelashes comprising applying the composition of claim 1 to the eyelashes.

8. A method of making up lips comprising applying the composition of claim 1 to the lips.

9. A method of making up eyelashes comprising applying the composition of claim 3 to the eyelashes.

10. A method of making up lips comprising applying the composition of claim 3 to the lips.

11. The composition of claim 1, wherein the composition is anhydrous.

12. The composition of claim 1, wherein the oil-soluble polar modified polymer has from about 5% to about 30% maleic anhydride units.

13. The composition of claim 1, wherein the oil-soluble polar modified polymer has from about 10% to about 25% maleic anhydride units.

14. A composition consisting essentially of: (a) at least one polar modified polymer selected from the group consisting of (1) a polar modified polymer consisting essentially of C26-C28 units and modified with at least one maleic anhydride unit, and having a weight-average molecular weight of less than or equal to 30000g/mol and a crystallinity of 8% to 60%; (2) a polar modified polymer consisting essentially of C2-C4 units and modified with at least one maleic anhydride unit, and having a weight-average molecular weight of less than or equal to 25 000g/mol and a melting point above 75° C., and mixtures thereof; (b) at least one tackifier, wherein the tackifier is a hydrocarbon resin; (c) at least one block copolymer, wherein the at least one block copolymer comprises styrene and is an A-B polymer or an A-B-A polymer, where A represents a hard segment and B represents a soft segment, and optionally at least one coloring agent, alkyl silsesquioxane resin, and a combination thereof, wherein the at least one tackifier and the at least one block copolymer form a pressure sensitive adhesive, and wherein the composition does not comprise a plasticizer.

15. The composition of claim 14, wherein the composition is an emulsion.

16. The composition of claim 14, wherein the at least one polar modified polymer is a wax consisting essentially of polypropylene and maleic anhydride units.

17. The composition of claim 14, wherein the at least one polar modified polymer is a wax consisting essentially of C26-C28 alpha olefin and maleic acid anhydride units.

18. A method of making up eyelashes comprising applying the composition of claim 14 to the eyelashes.

* * * * *